US006084089A

United States Patent [19]
Mine et al.

[11] Patent Number: 6,084,089
[45] Date of Patent: Jul. 4, 2000

[54] COLD-INDUCIBLE PROMOTER SEQUENCES

[75] Inventors: Toshiki Mine; Akio Ohyama; Toru Hiyoshi; Keisuke Kasaoka, all of Iwata-gun, Japan

[73] Assignee: Japan Tobacco, Inc., Tokyo, Japan

[21] Appl. No.: 08/894,731

[22] PCT Filed: Dec. 26, 1996

[86] PCT No.: PCT/JP96/03822

§ 371 Date: Oct. 27, 1997

§ 102(e) Date: Oct. 27, 1997

[87] PCT Pub. No.: WO97/24449

PCT Pub. Date: Jul. 10, 1997

[30] Foreign Application Priority Data

Dec. 27, 1995 [JP] Japan .................................. 7-351825

[51] Int. Cl.[7] .......................... C07H 21/04; C07H 21/02; C12Q 1/68
[52] U.S. Cl. ....................... 536/24.1; 536/23.6; 536/24.3; 435/6
[58] Field of Search .................................. 536/24.3, 23.6, 536/24.1; 935/6, 8; 435/6

[56] References Cited

U.S. PATENT DOCUMENTS 5,648,249 7/1997 Barry et al. ........................... 435/172.3

FOREIGN PATENT DOCUMENTS

WO 90/12876 11/1990 WIPO.

OTHER PUBLICATIONS

Yamaguchi–Shirozaki et al. Plant Cell. 6:251–264, Feb. 1994.
Qoronfleh et al. J. Bacteriol. 174:7902–7909, Dec. 1992.
Welin et al. Plant Molecular Biology 26:131–144, Oct. 1994.
Houde et al. Plant Physiol. 99:1381–1387, Oct. 1991.
Kurkela et al. Plant Molecular Biology 15:137–144, Jul. 1990.
Baker et al. Plant Molecular Biology 24:701–713, Mar. 1994.
Rocha–Sosa et al., The EMBO Journal, vol. 8, No. 1, pp. 23–29 (1989).
Wenzler et al., Plant Molecular Biology, 12:41–50 (1989).
Zhu et al., Plant Molecular Biology, 21:729–735 (1993).
van Berkel et al., Plant Physiol. 104:445–452 (1994).
Goring et al., Proc. Natl. Acad. Sci. USA, vol. 88, pp. 1770–1774 (Mar. 1991).
Ovalle et al., Plant Science 108, pp. 133–141 (Apr. 1995).
Brisson et al., The Plant Cell, vol. 1, pp. 559–566 (May 1989).
Sonnewald et al., Plant Molecular Biology 27:567–576 (1995).
Stark et al., Science, vol. 258, pp. 287–292 (Oct. 1992).
Sonnewald et al., The Plant Journal, 1(1), pp. 95–105, (1991).
Sonnewald, The Plant Journal, 2(4), pp. 571–581 (1992).
Jelitto et al., Planta 188:238–244 (1992).
Sun et al., The Plant Cell, vol. 4, pp. 119–128 (Feb. 1992).
Murata et al., Nature, vol. 356, pp. 710–713 (Apr. 1992).
Usami et al., Plant Molecular Biology 27:969–980 (1995).
Church et al., Proc. Natl. Acad. Sci. USA, vol. 81:1991–1995 (Apr. 1984).
Mori et al., The Journal of Biological Chemistry, vol. 266, No. 28, pp. 18446–18453 (1991).
Bachem et al., Bio/Technology, vol. 12, pp. 1101–1105 (Nov. 1994).
Baudo et al., Plant Molecular Biology 30:331–336 (1996).
Japanese Reference, "Tissue Culture", vol. 19(10), 357–361 (1993).
Boothe et al., Plant Physiol. 113:367–376 (1997).
Schneider et al., Plant Physiol. 113:335–345 (1997).
EMBL accession ATCADINP, submitted Sep. 20, 1994 by Choi S et al. "Sequence of a cadmium–induced cDNA from *Arabidopis thaliana*."

*Primary Examiner*—Jeffrey Fredman
*Attorney, Agent, or Firm*—Birch, Stewart, Kolasch & Birch, LLP

[57] ABSTRACT

This invention discloses a novel cold-inducible promoter which induces gene expression at low temperatures in potato tubers but which is scarcely induced in organs other than tuber or at normal temperature, which induces gene expression for a long time not less than five months. The promoters of this invention are the DNA sequence having a nucleotide sequence from first to 3546th nucleotide in the nucleotide sequence shown in SEQ ID NO: 1, or a part thereof having a cold-inducible promoter activity, or a DNA sequence having the same nucleotide sequence as said DNA sequences except that one or more nucleotides are deleted or substituted, or one or more nucleotides are inserted or added, which DNA sequence has a cold-inducible promoter activity and the DNA sequence having a nucleotide sequence from first to 4120th nucleotide in the nucleotide sequence shown in SEQ ID NO: 2, or a part thereof having a cold-inducible promoter activity, or a DNA sequence having the same nucleotide sequence as the said DNA sequences except that one or more nucleotides are deleted or substituted, or one or more nucleotides are inserted or added, which DNA sequence has a cold-inducible promoter activity.

3 Claims, 1 Drawing Sheet

Process for Preparing Construct in Which LCIP2-10 is Introduced
A:Asp718, B:BamHI, H:HindIII, Sm:SmaI, Sl:SalI, X:XbaI, Xh:XhoI
▓ Promoter Region

SEQUENCE LISTING

```
<160> NUMBER OF SEQ ID NOS: 8

<210> SEQ ID NO 1
<211> LENGTH: 3600
<212> TYPE: DNA
<213> ORGANISM: Solanum tuberosum

<400> SEQUENCE: 1
gatctatgat attcctttat caaattttag actaaggaag gattaatgat aagttttgaa        60
tatttgtttc caagataaat taaagttaac aagtcttatc attggattct taaagaagat       120
ttttataatg ttgcatcact tgttacgatt gacctaaaaa ttgttgtgta ctattttgat       180
ttattgagaa acgaatcat  tgttgtatag ggtaaaaatg ggttggacat cactactaaa       240
aataatggaa aaatcgacga ataaggtgag tctaaaaatt gacaatgttc atcgattttt       300
tttcatgcaa aaattataat ttcttaattt ttttttttt  aaatgataca gttccttggt       360
ttcaattaat tccatacaaa attgacgaac atgatcagtt cccggagtgt aaacctacag       420
ttgaatatta taaataaaaa cgatgaaata ttttatgaga acatgtatgg atcgagtggt       480
agaattttcc aaattcctaa aaaatacttg gattcacttc caaataggta cattctatag       540 gtatatttt  tgaaaaaacg atgacactat caatagctaa gtgaatatta atgttgtttt       600
aacaaagcac gatattgcta taacaatttt ttttttttgg tcaaaataaa ttcaaatgta       660
```

-continued

```
ccattttcat ggtaaacaca atattgccat aacaatttgt ttttaataaa cgagattgtt      720
atcaagaaat tttagttagc gatataaacg tgaccatgct acatttttt tttaaccttt       780 gaactttaat ttatcaactt caagttaaaa gtgagtgaat tcttttgagt tctagagttt      840
gtgcagtgtt tggattttg aaaacatttc atttgctacc acgatgatct caccctccaa       900
ttaggtggcc ctttctttac cgtccgatca tttggtactc tacattttg tcataaactt       960 tcaatttgat cattgaacag tcaaatatat ttaatcttta ggccaaatac atatagacaa     1020
cacattttag agatggtttg acttttgact tttggattta taagccaaaa gtaataaatt     1080
aaaacatttt agcttacttt tactatttta ctttaaaatc aaatggttat aagcacttt      1140 tttaaaaaat ttattcaaac acactaaaat gctttaaaac actcaagaga aattaattca     1200
catagacttt ggtttcaatt tttattttgg gcactcatca accttatttc attttatt      1260 taatctttca atttattttt tcatctatca tctaagcacg aaaaatatta ttaaatgtaa     1320
attgttcagt aaataacgtc atgtatttca ttttttttt tgtatgtcat cttggtcttc      1380
tgcatttaac ccaaatatcc aaaagaaat ttatattaac ttagctcaca attgataaaa      1440
acaacctatc ttcaatacag gtaaaagaa aaacaaactt cggttcacta ttaataaaaa     1500
tactaaaatg cgacgagctc cgtggggtta tgaacattta aaaataaat aaaaaaattc     1560 gtactttcat ccattgcttt tttcataaaa atatacagaa actataaata attattttta    1620
aaactctttc ttgaatcaac aaacaaattg attgagaaat ccaaattgat cgatgtgcat    1680
cgattttttt attaaaatat taacagattt ctgtcacatg tataaataat acataaaaat    1740
agaataaggt taacatttag tgccaatatt taaaatgtgg ataaattaaa ggggtgggtt    1800
tgtatatttg gtcttatctc taagtttta ttttgtcata catttaaaa ttgaaacttg      1860 agaaataatt ttaaaatata tacttaga tatatatttg aaaaaaattt aagtattgtg      1920
aatgaaagtc ccaaaattca aaactgatc aagacaattt tttaaaactt gaaaaatatt     1980
taaaacaatt tttcaaaatc tatagtcaaa taagtatttt tttttaaaaa aaaattcaaa    2040
aatctaattc taaatatata accaaaacta gcctcaattc atgaacttga ttggttacta    2100
ccactaccag catatatatt gttttatgag ctatatagtt caaaattggt gcatacttat    2160
caagaccggt atgagcctag attgagatgc tttgattatt attcctcgtt ttaaaataag    2220
tgaattattg tgataatata tttttattaa aaaattagat ataaattaaa tattatttt    2280 tatttttact cttttagtta ttttcaaact actcttaaaa taatataatt aatttcaaat   2340
aaactcataa atataaataa ttaaatctct ttaatcacct agcaaatgta aataaaagac   2400
aaaaaaaaaa gaaattttct agaactctct tggaacttcg aacaattcac atttaaaaaa   2460
aaaatgaaaa aaattcaaca attcactttt tttaaatgga aaagtatttt caattcgata   2520
agtaaatata atacgtgcaa tcgatttgtg aaatgtaaat atcaattggt taataaatta   2580
attaatcatt attattggaa ttcagttcct agcaatcttc tcaatatgtg ctccctaggt   2640
ccttttttct tgttatttt gataaattaa gaaaagata attttttatg gaaaaatgat     2700
ctgaaaaaaa tactaacttt ggctgaattt gatgttacga taccaaactt tcatgaggac   2760
ctattacccc ctaaaatatt taataccgta ttttttaccc cctgaactat ttaatagtgt   2820
attttgaagg tatatatgtg cccacgtgaa cacattacta tttataatta tgcaatattt   2880
tttatgtcca cgtgggcaca tatatatgtt aaaaatatgg tattaaatag tctaggggggt  2940 aataagtcct catgaaagtg tggtatcgta acaacaaatt tggccaaagt tgagtatttt   3000
tcagaccccc ttattcctat tttatctact atatcctcaa tttatttaga aagttgatat   3060
```

```
ttttgaaaaa aatgaaacct cttttaatga gtaaattaat ttaaattttt taacaattaa      3120
tagaaataaa ataataaatt tactatatca attattttt taacaaatat attaagtcaa       3180
agatgaataa gtaaatacta aatagtgaca gagcgtatat gaataagtaa atagtaagag      3240
agggagtata taactacata ttcgtaacgg aagcactaat tccaatgtgc ttttaacaga      3300
caacaattgt cgaaattgcg tgaattttat gtaaaggtac cataagtgaa caattcaaga     3360
agttttaggt tgtatatgct agatgaatta tctaagaggt acaagattaa aagtaatgaa     3420
ttactaaggg actacactgc aaatatcctt tcctataaat taacactcac cccaagcaca    3480
attttatcgt ctctttcaat tactttcact caaaaaaaaa aaggaaaaaa ttaagagtaa    3540 caaagatgt gtggaggtgc cataatctcc gattatgagc ccgccggaaa cttctaccgg     3600
```

<210> SEQ ID NO 2
<211> LENGTH: 4140
<212> TYPE: DNA
<213> ORGANISM: Solanum tuberosum

<400> SEQUENCE: 2

```
gatcaaataa ggttttcta aaagagaatt caaaatctaa ttttaaatat atagtcaaaa       60
ctagcttcaa ttcatgaact tgattggtta ctagttacta ccagtactag catatatatt    120
gttttatgag ctatagagtt taaaattggt gcatacttat ttatgaagac tggtatgtgc    180
ctagattgag atgctttgat tatattacac ctcatttag tgaattgctg aaacaatata     240
tatttattaa aaaaaattag ctataaatta gatattattt ttattttac cttttagtt     300 attttcaaat tatttttaaa aatataatta attcaaaata aactcatcaa tatagataat   360
taaatctctt gaaattatta cctagaaaaa tataaatgaa agacccaaat agaaaaatta   420
ataattcaat aactctcttg aactgtgaat aactcacttt ttttttaaa tatgaaaaaa    480 aaacactaca attcacttat tttgagatga taaaagtatt tcagtttcaa taagtgaata    540
taatatgtga agtgtgatac gtgaaatgta aatatcaagg ccagaaaact taagtataca    600
acttaataac tttaattacg cgaatatagc aatactttt ttttcaattg aatagcaata    660 ttttttttc caaactggaa ttcttattaa gaaaaaaaac gttttcagcc acaattatcc    720 atatcctta gattttctcca attattttac cttttcctgag ttacttcaat ttgttatata   780
tcatatccca taaaggaagg tttcctacca aaataaaact tctcttcaa acaaagatcg    840 acgatcaaat attcaaaccc aataattttt caatttaat tcatcacagc gggcattggg    900
actcatcagg taatcttttt ggtagtaatt cctttgattt tgtcgaattt ggtggaatat     960
acattcataa gattttggtt aatgttctgg tgcaactgta aaagggttaa ttattaaata    1020
gatattaaga tttagcaatt gtttgtggaa tattattagg attttcacat aatctgcgtt   1080
ttaattcttt ttggtattta ttcgttgttt tatattaacg ttttggtgt aatacaacaa     1140 catcatatga ttttggttgt aatatgatgc gtcgaataag tttttttata atttttttta   1200
ggttaattgg tatgttgcat gtcgaatgtt gacaaatttt atcaatagtt tcttttggta    1260
tgtgatgtgg tgtacacata caacttgaag ttaaatttca ggtatatatt tttgtgtatt    1320
tagttatatt atttggtata taaaatataa ctttaaaata atggttagtt ttttggtgta    1380
ttttatttat ccgaattggt tgaagataat aatttgaaaa ttggtcatat gtgatttggt     1440 acttaattg atatatttgt ttctataaat tgatggtaaa ttaaacttta gcaatgtgtt     1500
ggtgtatttt tgggttaaat gtcagattac ttttggtacg tcgattggtg taatacattg   1560
```

-continued

```
tatggtttaa ctgattgtgt gaattaccac agattggttt aagtatgtga tgtggtaaat    1620
gacaccaaaa taatactctg atgtatgagt tggtatattt attggtctaa tatataatac    1680
cataatttta aaataggttg ttgttgtgta aatagatatg ttaactatga aaaatattgc    1740
gtgaatgaat gcttcgtatg ttgtgtgaca caccaatttt aattaatttg attagataaa    1800
atgattgaag aattttgggt taaattatgg tgtatatctt ggtctagttt atgtatttcg    1860
tataatagtg cactatacac caccagttaa tcatgatgta caatactgtt caagatagca    1920
atgataaact atcatgtgca catgttttt taattaaagt tgaaaatggt aatttccttg    1980
gttagtttgt ggtgtatatg attggtgtat gtcatatatt aatatattag attgacctgt    2040
acaccaaaac atcaccatat tatgcaccaa agcgtcacca tactgtacac caaagtgtca    2100
ccatattata taccatttct aattaatttg taatttaaaa aattataaat aagtggttgt    2160
aatatgatgt tatacattgc ttgtaggtta gtatgtgtct aactatttat cgaaatgtat    2220
cgcaggaatt tatgtggatt tcaagattga aggagtgata catgacacaa acacccaaaa    2280
gacgtttacc aaatagatac aatactttgt aattaatttt atttttttat gaatgaaatt    2340
tttactaata ctagtgattt tttcatatat attggtataa ttatttatta attcaatgat    2400
aaatattgat agatagttga taatattatg gtgtaaggca acatatagtt ataatatata    2460
acaaaaatta atgttataat catgaatttt tacttcatgt gcaatttaat tatttgttgg    2520
tgtaagttat tcattgtgat taaaaataat tgtacaccaa acttaattta caatgtacat    2580
tatttaatat acttttttaa aaaagttaa aactattgaa tggtgctatg gtttataata    2640
ggaataaaat ttgattatat tttggtataa gttatatatt gtggttacaa aaaaaatggt    2700
caacaatata atacaaattc tataccattt aatatactca ccccccaccc caccccttt    2760 taactgacat atataaaatt gaagagagaa gtaaaaaaag atcttcccat aataattgaa    2820
atgaaatacc agagagaaaa aataaattca atagtaattg tatgaaatta atgagaaacg    2880
tgcttaacta tagaaatcat attaattaga tgatacattt ttactcccta aaaattagga    2940
catccaaatc taaaaagata ataagaacac acgtaattga agagagagag aaaattagca    3000
tcaaattcta aaaagataat taaaaacac gtaattgaag agagagaaaa aaattagcat    3060
ccaaatctaa aaaggataat tttaaaaaaa cgtaattgaa gagagagaaa atatttttt    3120 accatagtaa ttgtattaag taaaaagag aaaaaaaatc tttaagtaaa agaaatgtat    3180
gcaattataa ttgtgattga taatctaaat ggtaaaaata ataaataatg agttccataa    3240
aataagtcac taagccacaa aaataggtat aaaaacgtgt gagtgtgaag atatatatat    3300
ttaataagtt gtcatatttc taattaaaat gttattgtta taaataaaaa gagtttgaaa    3360
ctgtttagga gagagaatat ttgataatta ttaatatcct aattatactc catataaaag    3420
gcatgaaata ctaatagtat gagagagaaa aatctataaa accaaaatta aattaaatgt    3480
ttgttattat gtaatttaaa aacttagttt gtaattaaat ataaatatat tgatatttt    3540 gttaaataaa agtcttaagt agtatatttt tgtaattttc actaataata taatatcaat    3600
cgattgatga ataagtgact atattttat ttattatacc ctcaatttat ttagaaaatt    3660 aatgttttg aaaaagatgg aacctatttt aattagtaat taattttgaa ttttatcaa    3720 ttaataagag ccaaataata aattcattat atcaaatttt ttttattaat atatgtgttg    3780
aatcaaagat gaataagtaa atagtaacag aggaagtata tgactacata ttcgtaacgg    3840
aagcactagt tccaatgtac ttttaacgga caacaattgt cgaaattgcg tgaattttat    3900
gtaaaggtac caaaagtgaa catttcaaga agcttcaggt cgtatgtgcc agactaatta    3960
```

-continued

```
tcttggagga acaagattaa aattaataaa caactaaagg actaatctgc aaatatcctt      4020
tcctataaat taacactcac cccaagcaca attttatcgt ctctttcaat tactttcact      4080
caaaaaaaga aaaggaaat aaaaaaaaga gtaaaaaaag atgtgtggag gtgccataat       4140
```

<210> SEQ ID NO 3
<211> LENGTH: 1132
<212> TYPE: DNA
<213> ORGANISM: Solanum tuberosum
<220> FEATURE:
<221> NAME/KEY: CDS
<222> LOCATION: (45)..(836)

<400> SEQUENCE: 3

```
ctttcactca aaaaaaaaa ggaaaaaatt aagagtaaca aaag atg tgt gga ggt          56
                                              Met Cys Gly Gly
                                               1 gcc ata atc tcc gat tat gag ccc gcc gga aac ttc tac cgg aaa ctc         104
Ala Ile Ile Ser Asp Tyr Glu Pro Ala Gly Asn Phe Tyr Arg Lys Leu
 5                  10                  15                  20 tct gct cgt gac ctg tgg gct gag ctg gac cct atc tcc gac tac tgg         152
Ser Ala Arg Asp Leu Trp Ala Glu Leu Asp Pro Ile Ser Asp Tyr Trp
             25                  30                  35 tcc tct tcc tcc tca tcc tca act gtc gaa aac cct tat tcc gct cag         200
Ser Ser Ser Ser Ser Ser Ser Thr Val Glu Asn Pro Tyr Ser Ala Gln
         40                  45                  50 tcg ccg gtg act cac tcc gtc gat aag cct aag aaa tca gat tcc ggc         248
Ser Pro Val Thr His Ser Val Asp Lys Pro Lys Lys Ser Asp Ser Gly
     55                  60                  65 aaa tct aat caa ctc aaa aaa ggt aat aag act gtg aag gtt gag aag         296
Lys Ser Asn Gln Leu Lys Lys Gly Asn Lys Thr Val Lys Val Glu Lys
 70                  75                  80 gag aag agt act gga cca agg cag aga aag aac aag tac aga gga ata         344
Glu Lys Ser Thr Gly Pro Arg Gln Arg Lys Asn Lys Tyr Arg Gly Ile
 85                  90                  95                 100 agg cag aga cca tgg gga aaa tgg gct gct gag att cgc gat cct cag         392
Arg Gln Arg Pro Trp Gly Lys Trp Ala Ala Glu Ile Arg Asp Pro Gln
            105                 110                 115 aag ggt gtc cgt gtt tgg ctt ggt aca ttc aac aca gca gag gat gct         440
Lys Gly Val Arg Val Trp Leu Gly Thr Phe Asn Thr Ala Glu Asp Ala
        120                 125                 130 gcc aga gcc tat gat gag gct gct aag cgc att cgt ggt aac aag gcc         488
Ala Arg Ala Tyr Asp Glu Ala Ala Lys Arg Ile Arg Gly Asn Lys Ala
    135                 140                 145 aaa ctc aac ttc cct gcc cca tca cca cct gct aag cga cag tgc act         536
Lys Leu Asn Phe Pro Ala Pro Ser Pro Pro Ala Lys Arg Gln Cys Thr
150                 155                 160 agc act gtc gct gct gat cct cca cca gca cta ctc ctt gag agt tct         584
Ser Thr Val Ala Ala Asp Pro Pro Pro Ala Leu Leu Leu Glu Ser Ser
165                 170                 175                 180 aac ata ata tct tat aac aat tct cct tta atg aac ttc gga tat gat         632
Asn Ile Ile Ser Tyr Asn Asn Ser Pro Leu Met Asn Phe Gly Tyr Asp
            185                 190                 195 gtt cag agc caa act ccc tac tac cca atg gaa atg ccc gtt gct agt         680
Val Gln Ser Gln Thr Pro Tyr Tyr Pro Met Glu Met Pro Val Ala Ser
        200                 205                 210 gat gat tat gaa ctc aag gaa cag att tcc aac ttg gaa tcg ttc ctg         728
Asp Asp Tyr Glu Leu Lys Glu Gln Ile Ser Asn Leu Glu Ser Phe Leu
    215                 220                 225 gaa ttg gag cca gca gat tca tct gat cag ttt tca ggg atc gtc gat         776
Glu Leu Glu Pro Ala Asp Ser Ser Asp Gln Phe Ser Gly Ile Val Asp
```

```
                                                                              -continued Glu Leu Glu Pro Ala Asp Ser Ser Asp Gln Phe Ser Gly Ile Val Asp
        230                 235                 240 cct gat cct ctt aat gtt ttt ctg atg gag gat ttt gct tca act cag        824
Pro Asp Pro Leu Asn Val Phe Leu Met Glu Asp Phe Ala Ser Thr Gln
245                 250                 255                 260 cat cag ttc tat tgatcctgag ttgtttggtg agtgatgagt gactagttta            876
His Gln Phe Tyr ttagcttttg gctgtagtag tagtaataga gaaaaaagta catatgatat gataataata      936
agttgcgtgc cttagcctgc aattgtaata gtatcaatgt ttgttgtctt gtgttgttta      996
tgctttctaa atcttggatt taccttataa tgtttggtca tttggtgtat gtattgtaac     1056
tatatatgga gtactttatt actaaaaaaa aaaaaaaaaa aaaaaaaaaa ataaaaaaaa     1116
aaaaaaaaaa aaaaa                                                     1132

<210> SEQ ID NO 4
<211> LENGTH: 264
<212> TYPE: PRT
<213> ORGANISM: Solanum tuberosum

<400> SEQUENCE: 4

Met Cys Gly Gly Ala Ile Ile Ser Asp Tyr Glu Pro Ala Gly Asn Phe
 1               5                  10                  15

Tyr Arg Lys Leu Ser Ala Arg Asp Leu Trp Ala Glu Leu Asp Pro Ile
             20                  25                  30

Ser Asp Tyr Trp Ser Ser Ser Ser Ser Ser Thr Val Glu Asn Pro
         35                  40                  45

Tyr Ser Ala Gln Ser Pro Val Thr His Ser Val Asp Lys Pro Lys Lys
     50                  55                  60

Ser Asp Ser Gly Lys Ser Asn Gln Leu Lys Lys Gly Asn Lys Thr Val
 65                  70                  75                  80

Lys Val Glu Lys Glu Lys Ser Thr Gly Pro Arg Gln Arg Lys Asn Lys
                 85                  90                  95

Tyr Arg Gly Ile Arg Gln Arg Pro Trp Gly Lys Trp Ala Ala Glu Ile
            100                 105                 110

Arg Asp Pro Gln Lys Gly Val Arg Val Trp Leu Gly Thr Phe Asn Thr
        115                 120                 125

Ala Glu Asp Ala Ala Arg Ala Tyr Asp Glu Ala Ala Lys Arg Ile Arg
    130                 135                 140

Gly Asn Lys Ala Lys Leu Asn Phe Pro Ala Pro Ser Pro Pro Ala Lys
145                 150                 155                 160

Arg Gln Cys Thr Ser Thr Val Ala Ala Asp Pro Pro Ala Leu Leu
                165                 170                 175

Leu Glu Ser Ser Asn Ile Ile Ser Tyr Asn Asn Ser Pro Leu Met Asn
            180                 185                 190

Phe Gly Tyr Asp Val Gln Ser Gln Thr Pro Tyr Tyr Pro Met Glu Met
        195                 200                 205

Pro Val Ala Ser Asp Asp Tyr Gly Leu Lys Glu Gln Ile Ser Asn Leu
    210                 215                 220

Glu Ser Phe Leu Glu Leu Glu Pro Ala Asp Ser Ser Asp Gln Phe Ser
225                 230                 235                 240

Gly Ile Val Asp Pro Asp Pro Leu Asn Val Phe Leu Met Glu Asp Phe
                245                 250                 255

Ala Ser Thr Gln His Gln Phe Tyr
            260
```

```
<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 5
gaaaaaggaa ataaaaa                                                    17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Synthetic
      Olgionucleotide

<400> SEQUENCE: 6
gaaaaaatta agagtaac                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:Synthetic
      olgionucletotide

<400> SEQUENCE: 7
atcactagca acgggcat                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:210A primer

<400> SEQUENCE: 8
gttactctta attttttc                                                   18
```

COLD-INDUCIBLE PROMOTER SEQUENCES

This application is the national phase under 35 U.S.C. §371 of PCT International Application No. PCT/JP96/03822 which has an International filing date of Dec. 26, 1996 which designated the United States of America.

TECHNICAL FIELD

The present invention relates to a promoter sequence which induces expression of genes at low temperatures. The cold-inducible promoter sequence according to the present invention is useful for decreasing the amount of the reducing sugar in potato tubers during storage of potatoes at low temperatures, for inhibition of germination of potato tubers, for giving cold-resistance to plants, and the like.

BACKGROUND ART

It is indispensable to many crops to keep their qualities for a long time after harvest by storing them at a cold place or the like. However, it is known that if potato tubers are stored at a low temperature, accumulation of reducing sugar occurs, which is called low temperature sweetening, and the generated reducing sugar causes a coloring reaction (Maillard reaction) during processing them to French fried potatoes, potato chips or the like, so that the values of the commercial products are largely decreased. It is also known that fruits are softened by generation of ethylene. To overcome these problems, post-harvest physiology is now widely studied throughout the world.

In specifically expressing a foreign gene in potato tubers, the promoter of the gene for a storage protein patatin has been widely used in the world (EMBO J. 8(1): 23–29, 1989, Plant Mol. Biol. 12:41–50, 1989, Bio/Technology 12: 1101–1105, 1994 and so on). Expression of patatin gene increases with the development of the tuber. However, in the stage in which the tubers are developed, various metabolic systems such as that for converting reducing sugar to starch are activated. Therefore, it is possible that the gene ligated to the patatin promoter may disturb a metabolic system, which may lead to decrease in the yield. To avoid such a problem, it is thought necessary to isolate and utilize a promoter which efficiently promotes the expression of genes only in tubers stored at low temperatures and hardly promotes the expression of genes in the plant under normal conditions.

A number of types of cold-inducible genes from prokaryotic and eukaryotic organisms have been reported (There are reviews including Tissue Culture, 19(10): 357–361, 1993). Cold-inducible genes have also been isolated from potato tubers (Plant Physiol. 104: 445–452, 1994). It has been reported that an osmotin-like gene is isolated from a wild potato species, and that its expression is induced at low temperatures (Plant Mol. Biol. 21:729–735, 1993). The above-mentioned report is the only one which reports isolation of cold-inducible genes from potato tubers.

Five types of cold-inducible genes (cDNAs) have been isolated from potato tubers (Plant Physiol. 104: 445–452, 1994). Two of them have similarities to genes for known small heat-shock proteins, or to genes for cold-inducible proteins and ABA-inducible proteins of other plants. Other three genes have not been sequenced. The genomic DNAs (including promoters) of these cDNAs have not been isolated. It is thought that all of these genes quickly (within one week) respond to low temperatures.

Needless to say, promoters of the above-described known genes can be applied to crops (such as potato) which are required to be stored at a low temperature. However, it is not known whether these promoters (Plant Physiol. 104: 445–452, 1994 or the like) induce high expression in the desired organ alone (it is possible that these promoters are induced also in other organs at low temperatures). Further, genes controlled by these promoters may be expressed at normal temperature to a certain degree. Thus, it is not known whether efficient expression may be carried out only in the organs to be stored at a low temperature, such as potato tubers. Further, although potato tubers are stored for as long as several months, it is not known whether the above-described promoters function for such a long time (Plant Physiol. 104: 445–452, 1994. In this reference, the promoter activities are tested for only about one month).

DISCLOSURE OF THE INVENTION

An object of the present invention is to provide a novel cold-inducible promoter which induces gene expression at low temperatures in potato tubers but which is scarcely induced in organs other than tuber or at normal temperature, which induces gene expression for a long time not less than five months.

Another object of the present invention is to provide a DNA fragment useful as a probe for discovering novel cold-inducible promoter existing in potato or other plants.

The present inventors intensively studied to discover a promoter sequence which is induced at low temperatures in potato tubers but which is scarcely induced in organs other than tuber or at normal temperature, which induces gene expression for a long time not less than five months, thereby completing the present invention.

That is, the present invention provides a DNA sequence having a nucleotide sequence from first to 3546th nucleotide in the nucleotide sequence shown in SEQ ID NO: 1, or a part thereof having a cold-inducible promoter activity, or a DNA sequence having the same nucleotide sequence as the above-mentioned DNA sequences except that one or more nucleotides are deleted or substituted, or one or more nucleotides are inserted or added, which DNA sequence has a cold-inducible promoter activity.

The present invention also provides a DNA sequence having a nucleotide sequence from first to 4120th nucleotide in the nucleotide sequence shown in SEQ ID NO: 2, or a part thereof having a cold-inducible promoter activity, or a DNA sequence having the same nucleotide sequence as the above-mentioned DNA sequences except that one or more nucleotides are deleted or substituted, or one or more nucleotides are inserted or added, which DNA sequence has a cold-inducible promoter activity.

By the present invention, a promoter sequence which is induced at low temperatures in potato tubers but which is scarcely induced in organs other than tuber or at normal temperature, which induces gene expression for a long time not less than five months, was provided. By utilizing the promoter sequence according to the present invention, reduction of the amount of the reducing sugar in potato tubers during storage of potatoes at low temperatures, inhibition of germination of potato tubers, and giving cold-resistance to plants, and the like may be attained.

BEST MODE FOR CARRYING OUT THE INVENTION

Figure 1:
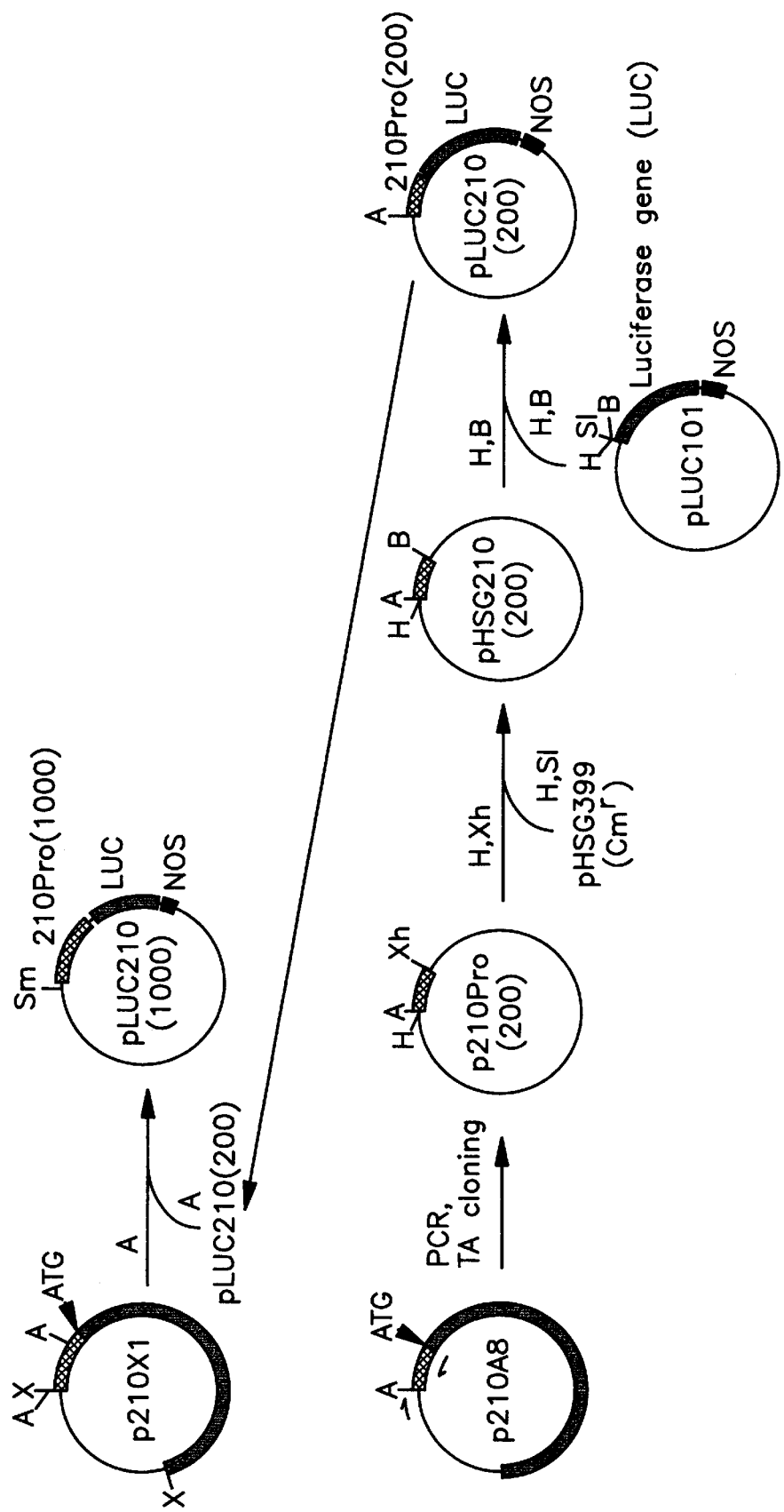
FIG. 1 is a drawing for explaining the preparation process of a construct in which LCIP2-10 promoter is introduced.

The cold-inducible promoter sequence according to the present invention is contained in the region from the first to 3546th nucleotide in the nucleotide sequence shown in SEQ ID NO: 1 in the Sequence Listing, or in the region from the first to 4120th nucleotide in the nucleotide sequence shown in SEQ ID NO: 2. Each of these sequences exhibits cold-inducible promoter activity in its entirety. However, parts of these sequences, which exhibit cold-inducible promoter activities, e.g., the region from 2418th to 3541st nucleotide of the nucleotide sequence shown in SEQ ID NO: 1 in the Sequence Listing, are also within the scope of the present invention. Further, sequences containing the region from 2418th to 3541st nucleotide of the nucleotide sequence shown in SEQ ID NO: 1, which have cold-inducible promoter activities, are also within the scope of the present invention.

The "ATG"s at 3547th to 3549th nucleotide in the sequence shown in SEQ ID NO: 1 in the Sequence Listing and at 4121st to 4123rd nucleotide in the sequence shown in SEQ ID NO: 2 in the Sequence Listing are translation initiation codons. The mRNA (cDNA) sequence of the 3503rd nucleotide and downstream thereof of the sequence shown in SEQ ID NO: 1 is shown in SEQ ID NO: 3 together with the deduced amino acid sequence (SEQ ID NO: 4) encoded thereby.

In the present specification, the term "cold-inducible" means that expression of a gene by the promoter is induced at a temperature not higher than 6° C., and by keeping the temperature of not higher than 6° C., the expression is maintained for not less than 5 months.

It is well-known in the art that there are cases wherein the physiological activity of a physiologically active DNA sequence is retained even if the nucleotide sequence of the DNA is modified to a small extent, that is, even if one or more nucleotides are substituted or deleted, or even if one or more nucleotides are added or inserted. Therefore, DNA fragments having the same nucleotide sequence as the above-mentioned cold-inducible promoter sequences according to the present invention except that the DNA fragments have such modifications, which have the cold-inducible promoter activities, are included within the scope of the present invention. That is, the DNA fragments having the same nucleotide sequence as the region from the first to 3546th nucleotide of the sequence shown in SEQ ID NO: 1 or a part thereof having the cold-inducible promoter activity except that one or more nucleotides are deleted or substituted, or one or more nucleotides are inserted or added, which have the cold-inducible promoter activities, are included within the scope of the present invention. Further, DNA fragments having the same nucleotide sequence as the region from the 2417th to 3541st nucleotide of the sequence shown in SEQ ID NO: 1, which region is a part of the above-mentioned region, or a part thereof having the cold-inducible promoter activity except that one or more nucleotides are deleted or substituted, or one or more nucleotides are inserted or added, which have the cold-inducible promoter activities, are included within the scope of the present invention.

Similarly, DNA fragments having the same nucleotide sequence as the region from the first to 4120th nucleotide of the sequence shown in SEQ ID NO: 2 or a part thereof having the cold-inducible promoter activity except that one or more nucleotides are deleted or substituted, or one or more nucleotides are inserted or added, which have the cold-inducible promoter activities, are included within the scope of the present invention.

Modification of DNA which brings about addition, insertion, deletion or substitution can be attained by the site-specific mutagenesis which is well-known in the art (e.g., Nucleic Acid Research, Vol. 10, No. 20, p6487–6500, 1982). In the present specification, "one or more nucleotides" means the number of nucleotides which can be added, inserted, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting or adding one or more nucleotides without losing the function include a method in which the gene is treated with a mutagen and a method in which the gene is selectively cleaved, a selected nucleotide is removed, added or substituted and then the gene is ligated.

As detailed in the examples described below, the nucleotide sequences shown in SEQ ID NOS: 1 and 2 were determined by the following steps:

(1) A cDNA library originated from tubers stored at 4° C. for a long time was prepared. Then cDNA clones which did not hybridize (not stringent) with mRNAs of various growing potato tissues (leaf, stem, root, callus, and growing tuber) but hybridized with a mRNA in the tuber stored at a low temperature were isolated and their sequences were determined and analyzed.

(2) Northern analysis was carried out using the RNAs used in (1) to confirm again that transcripts corresponding to the isolated clones were not substantially expressed in potato plants under normal condition.

(3) Tubers after harvest were stored at various temperatures (3, 6, 9, 12, 15, 20° C.) for a long time (5–6 months). Using RNAs extracted from these tubers, it was checked by Northern analysis whether the expression was induced at a low temperature, at what temperature was the expression induced, how long was the gene expressed, and whether the expression was stopped by restoring the temperature to normal temperature. As a result, it was confirmed that the transcript homologous to the cloned cDNA was induced at a low temperature not higher than 6° C., was expressed for a long time (at least 5–6 months), and the expression was stopped by restoring the temperature to normal temperature.

(4) Using potato plants in vitro, it was checked whether expression of the gene was induced at a low temperature in tissues other than tuber. As a result, although it was possible that induction occurred in tissues other than tuber, the level of expression was thought to be insubstantial (the change was extremely smaller than in the tuber stored at a low temperature).

(5) By Southern analysis, it was confirmed that each of the genes was a single copy gene. The band was not detected in rice, maize, tobacco or the like, but detected in tomato.

(6) Two genomic clones were isolated. The sequence in the vicinity of ATG initiation codon of one of the genomic clones was completely identical to the sequence in the cDNA. The sequence of another genomic clone was not completely identical to the sequence of the cDNA. However, since the homology was high, it was thought that each clone encoded a gene having the same function but located at a different locus. The expression patterns of the two genes analyzed by reverse transcription PCR were thought to be substantially identical.

(7) Nucleotide sequences of the region upstream of the ATG of the genomic clones were analyzed. As a result, the ABA induction (reaction) motif which was often observed in cold-inducible gene was not observed but GA reaction motif was observed in both clones. The isolated two genomic clones had a high homology (80.3%) up to 500 bp upstream of the ATG, but no regions having high homology were observed upstream thereof.

(8) A part of the promoter sequence of one of the isolated two genomic clones was introduced into potato using luciferase gene (Science 234: 856–859, 1986) as a reporter. The microtubers produced in the obtained transformants were subjected to cold storage test to confirm the cold-inductivity of the promoter. The cold-inductivity was also observed, although slightly, in the leaves of the transformants.

The promoter sequence according to the present invention may be obtained by the process detailed in the examples below, which process comprises the steps of (1) to (8). Further, since the nucleotide sequence of the promoter sequence was determined by the present invention, a DNA containing the promoter sequence may easily be obtained by the PCR or the like using potato genome as the template.

The sequences shown in SEQ ID NOS: 1 and 2 do not have homology with known cold-inducible genes originated from potato tuber. Therefore, the promoter sequences according to the present invention are thought to be novel promoter sequences of a new type which is different from the known promoter sequences.

Expression of a gene by the cold-inducible promoter sequence according to the present invention in leaf, root, stem and tuber of a potato growing at normal temperature (20° C.) is very weak. Expression is induced by placing the harvested tuber at low temperatures (6° C. or lower). Although expression is induced by placing an organ (leaf, stem or root) other than tuber at low temperatures, the expression is slight. However, expression is induced considerably in the sprout germinated from the cold-stored tuber. On the other hand, the report (Plant Physiol. 104: 445–452, 1994) is silent about the expression in organs other than tuber. Although the gene according to the present invention is not, in a strict sense, a gene specific to cold-stored tuber, it is close thereto, and is a gene (promoter) useful for maintaining the quality after harvest.

By the cold-inducible promoter sequence according to the present invention, gene expression is induced at low temperatures and is stopped by restoring the temperature to normal temperature. According to the classification by a reference (Plant Physiol. 104: 445–452, 1994), the gene is thought to be classified into the group which is slow to react to low temperature (The expression does not reach plateau within about one week from the beginning of the cold treatment. Van Berkel et al. (Plant Physiol. 104: 445–452, 1994) did not succeed in isolation of a gene belonging to this group). Therefore, expression can be controlled by controlling temperature.

The cold-inducible promoter sequence according to the present invention induces expression for a long time (at least 5 months) during cold-storage. On the other hand, the report (Plant Physiol. 104: 445–452, 1994) is silent about the long-term expression of the reported gene. By using the promoter sequence according to the present invention, long-term control of a gene can be attained.

In rice, maize and tobacco, no genes having high homology with the gene according to the present invention were found. In tomato, such a gene was found. Therefore, by using the promoter according to the present invention in gene introduction into rice, maize, tobacco or the like, gene expression with low gene silencing (Proc. Natl. Acad. Sci. USA, 88: 1770–1774, 1991) may be attained.

Thus, the cold-inducible promoter according to the present invention may be applied to the following uses:

(i) Control of Amount of Reducing Sugar in Potato Tubers during Cold-Storage (Reduction of Amount of Reducing Sugar)

The amount of the reducing sugar in the potato tubers stored at a low temperature may be reduced by ligating to the downstream region of the promoter sequence according to the present invention, for example, an acid invertase inhibitor (Ovalle et al., Plant Science 108 (1995) 133–141) gene, antisense gene of vacuolar acid invertase (EMBL Data Library accession number X76946), PFK (EC 2.7.1.11, WO95/05457) gene, antisense gene of starch phosphorylase (Brisson et al., Plant Cell 1 (1989) 559–566; Mori et al., J. Biochem 266 (1991) 18446–18453, Sonnwald et al. Plant Mol. Biol. 27 (1995) 567–576), antisense gene of β- or α-amylase (Kreiberg and Gaushing, 12th Triennial Conference of the European Association for Potato Research, Abstracts (1993) 334–335), ADP glucose pyrophophorylase (Stark et al., Science 258 (1992) 287–292) gene or the like. By this, coloring of French fried potatoes or potato chips made from potato tubers can be prevented.

(ii) Inhibition of Germination of Potato Tubers

The promoter according to the present invention has a property to induce expression at low temperatures and to stop expression when returned to normal temperature. Therefore, by ligating therewith, for example, an yeast invertase gene (Sonnewald et al. Plant J. 1 (1991) 95–100), E. coli inorganic pyrophosphatase gene (Sonnewald, Plant J. 2 (1992) 571–581; Jelitto et al. Planta 188 (1992) 238–244), antisense gene of ent-kaurene synthetase (participates in gibberellin biosynthesis, Sun et al. Plant Cell 4 (1992) 119–128) or the like, and introducing the ligated gene into a plant such as potato or onion, growth regulation such as to express the gene (not germinate) at a low temperature and to stop the expression (germinate) at normal temperature may be attained.

(iii) Giving Cold-Resistance to Plants

Cold-resistance may be given to plants by expressing, for example, glycerol-3-phosphate acyl transferase (Murata et al. Nature 356 (1992) 710–718) gene, Pyruvate, orthophosphate dikinase (PPDK, Usami et al. Plant Mol. Biol. 27 (1995) 969–980) gene originated from *Flaveria brownie,* or the like.

The probe for searching cold-inducible promoters, according to another aspect of the present invention, will now be described.

The probe according to the present invention is a DNA fragment having at least 15 consecutive nucleotides in the region from 45th to 839th nucleotide in the sequence shown in SEQ ID NO: 3 in the Sequence Listing or a sequence complementary thereto. It is highly probable that the sequence of the region from 45th to 839th nucleotide in the sequence shown in SEQ ID NO: 3 or a sequence having a high homology with this sequence exists at a downstream region of a cold-inducible promoter sequence. Therefore, by screening plant genomic DNAs using this sequence or a part thereof as a probe, novel cold-inducible promoter existing in potato or in other plants may be discovered.

The probe is designed based on the above-mentioned sequence and its size is at least consecutive 15 nucleotides. As long as its size is not less than 15 nucleotides, the probe may have any size up to the full length of the above-mentioned sequence. The probe may be either single-stranded or double-stranded, although the probe is single-stranded when it is used. DNA fragments having the same nucleotide sequence as the above-mentioned probe except that one or more nucleotides are added, deleted, inserted or substituted, which specifically hybridize with the above-mentioned sequence or a sequence having a high homology thereto, are also within the scope of the present invention. The addition, deletion, insertion or substitution of the nucleotides may be carried out in the same manner as described above for the cold-inducible promoter according to the present invention.

The probe according to the present invention can be prepared by digesting the DNA fragment shown in SEQ ID NO: 3 in the Sequence Listing obtained by the process detailed in the examples described below with an appropriate restriction enzyme. The probe may also be prepared by PCR using a sample containing the sequence. Alternatively, a single-stranded DNA to be used as the probe may be synthesized by a conventional method using a commercially available DNA synthesizer (e.g., one commercially available from Perkin Elmer).

The probe according to the present invention may be labeled with, for example, a radioisotope, detectable enzyme or the like by a conventional method. For example, when $^{32}P$ is used as the label, in cases where the DNA fragment shown in SEQ ID NO: 3 is labeled, it can conveniently be labeled by the random priming labeling, and in cases where a synthetic probe is labeled, it can conveniently be labeled by labeling the 5'-end thereof using a phosphorylating enzyme.

In using the probe, the hybridization may be carried out by a conventional method. In general, medium hybridization intensity (hybridization is carried out at 42–50° C. and washing is performed with 0.1×SSC) is employed.

If hybridization is observed when a genomic library of a target plant is screened with the probe according to the present invention, a novel cold-inducible promoter may be obtained by specifying the upstream region of the hybridized gene.

EXAMPLES

The present invention will now be described in more concretely by way of examples thereof. It should be noted, however, that the present invention is not restricted to the examples.

Example 1
Differential Screening (above-described step (1))

Total RNAs were extracted from potato tubers (variety: Toyoshiro) stored at 4° C. for 7 months by the SDS/phenol method, and polyA$^+$RNAs were purified using Dynabeads (Dynal). Using the obtained polyA$^+$RNAs, cDNAs were prepared and ligated to λgt10 vector to obtain a library (Amersham λgt10 cloning kit, Amersham Japan). The polyA$^+$RNAs used in the preparation of the library and polyA$^+$RNAs extracted from growing tubers were labeled with $^{32}P$, and differential screening was carried out.

Hybridization, washing and the like were performed as described in a reference (Proc. Natl. Acad. Sci. USA 81:1991–1995, 1984), and autoradiographs obtained by using the above-described two types of probes were compared. The cDNA clones whose signals were thought to be increased during storage were plated again using toothpicks and hybridization was carried out again. The signals in the autoradiographs were measured with a densitometer. Clones whose signals were prominently increased were first selected and a clone (CIP353) which did not hybridize with mRNAs in organs (leaf, stem, root and callus) other than tuber was isolated.

Example 2
Northern Blot Analysis (above-described steps (2) and (3))

Total RNAs were extracted from various potato tissues (tuber, leaf, stem and root of variety Toyoshiro and cultured cells of variety Kennebec) by the SDS-phenol method. The obtained RNAs were separated (3 μg/lane) by glyoxal gel electrophoresis (Molecular cloning: A Laboratory Manual/Second Edition, Cold Spring Harbor Laboratory, 1989) and transferred to Gene-screen Plus membrane (Du Pont). As a probe, EcoRI fragment (full length) of the cDNA (CIP353), which was labeled by the multiprimer method (Molecular cloning: A Laboratory Manual/Second Edition, Cold Spring Harbor Laboratory, 1989) was used. Transfer of the bands to the membrane, hybridization, washing and the like were carried out in accordance with the instructions attached to the Gene-screen membrane (Du Pont). The results are shown in Tables 1 to 3.

TABLE 1

Expression of mRNA in Various Organs and Suspended Cells of Potatoes

| Organ | mRNA Level |
|---|---|
| Leaf*1 | ± |
| Stem*1 | ± |
| Root*1 | ± |
| Suspended Cells*2 | ± |
| Growing Tuber | ± |
| Tuber Cold-Stored for 7 months | +++++ |

*1: originated from plantlets cultured in vitro
*2: variety Kennebec. For others, variety Toyoshiro was employed.

TABLE 2

Expression of mRNA in Stored (Short Time) Tubers

| Storage Period | 2 weeks | 4 weeks | 2 months | 3 months |
|---|---|---|---|---|
| 20° C. | ± | ± | ± | ± |
| 15° C. | ± | ± | ± | ± |
| 12° C. | ± | ± | ± | ± |
| 9° C. | ± | ± | ± | ± |
| 6° C. | ++ | ++ | +(+) | +(+) |
| 3° C. | +(+) | +++ | +++(+) | ++++ |

Stored at 20° C. for 1 week after stored at 6° C. for 2 months ±
Stored at 20° C. for 2 weeks after stored at 6° C. for 2 months ±
Stored at 20° C. for 4 weeks after stored at 6° C. for 2 months ±

TABLE 3

Expression of mRNA in Stored (Long Time) Tubers

| Storage Period | 3 months | 5 months | 6 months |
|---|---|---|---|
| 20° C. | − | − | ± |
| 6° C. | +(+) | +++ | +(+) |
| 3° C. | ++++ | +++++ | ++++ |

Stored at 20° C. for 1 month after stored at 3° C. for 5 months ±
Stored at 20° C. for 1 month after stored at 6° C. for 5 months ±
Stored at 3° C. for 1 month after stored at 20° C. for 5 months +++
Stored at 6° C. for 1 month after stored at 20° C. for 5 months +(+)
Sprout germinated from tuber stored at 20° C. for 5 months ±
Sprout germinated from tuber stored at 6° C. for 5 months +(+)

As is apparent from the tables, the above-mentioned probe did not substantially hybridize with the mRNAs in tubers, leaves, stems and roots of normally growing potatoes and in cultured cells. Further, hybridization was observed for the potato tubers stored for 5–6 months at a temperature not higher than 6° C., while hybridization was not substantially observed for the potato tubers stored for 5–6 months at a temperature not lower than 9° C.

Example 3
Confirmation of Tissue Specificity (the above-described step (4))

Sterile shoots cultured on Linsmaier and Skoog (Physiol. Plant, 18:100–127, 1965) agar medium at 20° C., 3000 lux, under illumination for 16 hours per day for 3–4 weeks were used as the materials. The shoots were placed at 3° C. or 20° C. and cultured under illumination for 16 hours per day at 3000 lux for 4 weeks. On 0, 2 and 4 weeks from the beginning of the culture, samples (leaf, stem and root separately) were taken, and RNAs were extracted therefrom. Northern analysis was performed as described above. The results are shown in Tables 4 and 5.

TABLE 4

Expression of mRNA in Various Organs Stored (20° C.)

| Storage Period | not stored | 2 weeks | 4 weeks |
|---|---|---|---|
| Leaf*1 | − | − | (±) |
| Stem*1 | − | − | (±) |
| Root*1 | (±) | ± | ± |

*1: originated from plantlets cultured in vitro

TABLE 5

Expression of mRNA in Various Organs Stored (3° C.)

| Storage Period | not stored | 2 weeks | 4 weeks |
|---|---|---|---|
| Leaf*1 | − | ± | ± |
| Stem*1 | − | ± | + |
| Root*1 | (±) | ± | ± |

*1: originated from plantlets cultured in vitro

As is apparent from the tables, although hybridization was slightly observed for leaf, stem and root stored at 3° C., the amount of the hybridized mRNA was much smaller than in the tubers stored at the same temperature.

Example 4
Southern Blot Analysis (above-described step (5))

DNAs were prepared by the hot phenol method from young leaves of potato variety Toyoshiro, tomato variety House Odoriko, tobacco variety F104, maize variety A188 and rice variety Asanohikari. The DNAs (10 μg) extracted from each of the varieties were digested with restriction enzyme EcoRI or HindIII (In the assay of copy number in the potato genome, BamHI, BglII, EcoRV and XbaI were also used in addition to the above-mentioned restriction enzymes. All of the restriction enzymes used were commercially available from Takara) and the resultant was subjected to agarose gel electrophoresis, followed by transferring the bands (Molecular cloning: A Laboratory Manual/Second Edition, Cold Spring Harbor Laboratory, 1989) to Hybond N$^+$ membrane (Amersham Japan). EcoRI fragment (full length) of the cDNA (CIP353), which was labeled by the multiprimer method, was used as the probe, and hybridization was carried out as in Example 1.

As a result, it was confirmed that the gene was a single copy gene. Further, bands were not observed for rice, maize and tobacco, and observed for tomato.

Example 5
Isolation of Genomic Clone (above-described step (6))

From young leaves of potato variety Toyoshiro, DNAs were extracted by the hot phenol method, and 100 μg of the obtained DNAs was partially digested with 0.0078 units or 0.0156 units of a restriction enzyme Sau3AI (Takara) for 1 hour (as the reaction buffer, the one enclosed in the commercial product of Takara was used). The reaction was stopped by EDTA at a final concentration of 40 mM and the reaction product was subjected to phenol/chloroform extraction and ethanol precipitation, followed by dissolving the digested DNAs in 150 μl of TE. The DNAs were treated at 65° C. for 10 minutes and overlaid on 10–40% sucrose density gradient (prepared by sequentially overlaying 40%, 32.5%, 25%, 17.5% and 10% sucrose solutions in a buffer containing 20 mM Tris, pH 8.0, 1 mM EDTA and 200 mM NaCl). The resultant was centrifuged at 20,000 rpm at 20° C. for 17 hours or more using Hitachi SRP28SA rotor, and fractionated to 0.5 ml each, followed by analysis on 0.5% agarose gel. The fractions containing DNA fragments having a size of not less than 15 kb were combined and concentrated by ethanol precipitation. Then 0.4 μg of aliquot of the resultant was ligated with 1 μg of λDASHII/BamHI (Stratagene) and the obtained product was subjected to packaging using GigapackII Gold (Stratagene). The ligation and packaging reactions were carried out in accordance with the instructions attached to the commercial product of Stratagene. About 800,000 clones were screened as in Example 1 with the probe which is the EcoRI fragment (full length) of the cDNA (CIP353), which was labeled by the multiprimer method (Molecular cloning: A Laboratory Manual/Second Edition, Cold Spring Harbor Laboratory, 1989), to obtain two positive clones (LCIP2-10 and LCIP1-2). Extraction of DNAs from the phage and subcloning to the plasmid vector were carried out as described in a reference (Molecular cloning: A Laboratory Manual/Second Edition, Cold Spring Harbor Laboratory, 1989).

Example 6
Reverse Transcription PCR Analysis (the above-described step (6))

As a result of analysis of the DNA sequences of the two genomic clones, difference in several nucleotides in the non-translational region upstream of the ATG was found. Thus, synthetic oligonucleotides 12S (5'-GAAAAAGGAAATAAAAA-3' (SEQ ID NO: 5), specific to mRNA originated from LCIP1-2; Tm=43° C.) and 210S (5'-GAAAAAATTAAGAGTAAC-3' (SEQ ID NO: 6), specific to mRNA originated from LCIP2-10, Tm=45° C.) were prepared, and reverse transcription PCR was performed using the synthetic oligonucleotides and a 3'-side antisense primer 325aR (used for both the two mRNAs, 5'-ATCACTAGCAACGGGCAT-3' (SEQ ID NO: 7), Tm=54° C.) originated from the inner sequence of the cDNA.

As the material for the reverse transcription PCR, 10 µg of the total RNAs originated from various tissues of potato variety Toyoshiro was used. The RNAs were mixed with 500 ng of oligo-dT (water was added to a total volume of 55 µl) and the obtained mixture was treated at 70° C. for 10 minutes. The resultant was mixed with a reaction solution (20 µl of 5x1st. strand buffer (BRL), 5 µl of 10 mM dNTPs, 10 µl of 100 mM DTT, 5 µl of RNase inhibitor (Pharmacia), and 5 µl of Superscript RTase (BRL) (total volume of 100 µl), and the obtained mixture was allowed to react at 37° C. for 1 hour, followed by treatment at 95° C. for 5 minutes to obtain single stranded cDNAs used as the templates in the reverse transcription PCR (the cDNA level in this solution was assumed to be 100 ng/µl).

Using 1–100 ng of the synthesized cDNAs as the templates, PCR reaction was performed (1–100 ng of cDNAs, 10 pmolx2 of primers, 1.6 µl of 2.5 mM dNTPs, 2 µl of 10xPCR buffer (Takara), 0.2 µl of rTaq (Takara), total volume of 20 µl). When the above-mentioned 12S and 325aR primers were used, the reaction was carried out by repeating 30 times the thermal cycle of 94° C. for 30 seconds, 45° C. for 30 seconds and 72° C. for 60 seconds. When the above-mentioned 210S and 325aR primers were used, the reaction was carried out by repeating 30 times the thermal cycle of 94° C. for 30 seconds, 47° C. for 30 seconds and 72° C. for 60 seconds. The PCR products were analyzed by agarose gel electrophoresis. The results are shown in Table 6. In this table, LCIP2-10 corresponds to the sequence shown in SEQ ID NO: 1 in the Sequence Listing hereinbelow described, and LCIP1-2 corresponds to SEQ ID NO: 2. As is apparent from the table, prominent expression was observed only for the tubers stored at low temperatures for a long time for both of the mRNAs originated from the genomic DNAs. From this, it is seen that both of the sequences shown in SEQ ID NOS: 1 and 2 have cold-inducible promoter activities.

TABLE 6

Expression of mRNAs Originated from Two Genomic DNAs Analyzed by RT-PCR

| | LCIP2-10 mRNA | LCIP1-2 mRNA |
| --- | --- | --- |
| Leaf*1 stored at 20° C. for 4 weeks | (±) | − |
| Stem*1 stored at 20° C. for 4 weeks | (±) | − |
| Root*1 stored at 20° C. for 4 weeks | (±) | (±) |
| Leaf*1 stored at 3° C. for 4 weeks | ± | (±) |
| Stem*1 stored at 3° C. for 4 weeks | + | (±) |
| Root*1 stored at 3° C. for 4 weeks | (±) | ± |
| Sprout germinated from tuber stored at 20° C. for 5 months | + | + |
| Sprout germinated from tuber stored at 6° C. for 5 months | +(+) | + |
| Growing tuber | (±) | ± |
| Mature tuber immediately after harvest | − | − |
| (Mature) tuber stored at 20° C. for 5 months | − | − |
| Tuber stored at 3° C. for 5 months | ++(+) | +++ |

*1: originated from plantlets cultured in vitro

Example 7
Determination and Analysis of DNA Nucleotide Sequences (the above-described steps (1) and (7))

The sequencing reaction and sequencing were carried out by the dideoxy method (ABI, Taq DyeDeoxy Terminator Cycle Sequencing Kit) employing a plasmid DNA as a template, using a DNA sequencer (ABI, 373A). Analysis of the sequences was carried out using a software GENETYX (Software Development Co., Ltd).

As a result, one of the two genomic clones contained the sequence shown in SEQ ID NO: 1 and the other clone contained the sequence shown in SEQ ID NO: 2. Further, the above-described cDNA clone (CIP353) contained the sequence shown in SEQ ID NO: 3.

Example 8
Construction of Vector for Transformation and Confirmation of Cold-inductivity of Promoter by Transformation Method (above-described step (8))

Genomic clone LCIP2-10 was digested with a restriction enzyme Asp718 (Boehringer) and Asp718 fragment containing about 200 bp upstream of the initiation ATG codon was introduced into a plasmid pUC19 to obtain a recombinant plasmid p210A8. Using this plasmid (p210A8) as a template and using M13 primer RV (Takara) and 210A primer (5'-GTTACTCTTAATTTTTTC-3' (SEQ ID NO: 8)), PCR (94° C. for 20 seconds, 55° C. for 30 seconds, 72° C. for 60 seconds, 25 cycles) was performed. The amplified product was subcloned into TA cloning vector (Invitrogen) to prepare a vector p210Pro(200) containing only about 200 bp upstream of the initiation ATG codon. From this vector, the fragment containing about 200 bp upstream of the initiation ATG codon was isolated by digestion with restriction enzymes HindIII and XhoI (Takara) and inserted into the HindIII, SalI site of pHSG399 (Takara) to obtain a plasmid pHSG210(200). This plasmid was digested with HindIII and BamHI (Takara) and the isolated fragment of about 200 bp upstream of the ATG codon was inserted into the 5' upstream region of a vector (pLUC101) prepared by substituting the β-glucuronidase gene of pBI101 vector (Clonetech) with a luciferase gene (Science 234: 856–859, 1986) to obtain pLUC210(200). On the other hand, XbaI (Takara) fragment containing about 1000 bp upstream of the initiation ATG codon of the genomic clone LCIP2-10 was inserted into pUC18 vector to obtain a vector (p210X1) and a fragment of 800 bp (about −200 to −1000 bp, upstream of ATG codon) was isolated from this vector by digestion with restriction enzyme Asp718. This fragment was inserted into the Asp718 site of pLUC210(200) to obtain a vector pLUC210(1000) for transformation, which vector contained the promoter region of about 1 kb and a luciferase gene as a reporter. The vectors for transformation (pLUC101 and pLUC210(1000)) were introduced into a bacterium Agrobacterium tumefaciens LBA4404 by triparental mating (Plant Gene Manipulation Manual, Kodansha, 1990) and the resultant was used for transformation of plants.

Transformation of potato was carried out in accordance with a reference (Japanese Laid-open Patent Application (Kokai) No. 6-133783). Stems and leaves of variety Toyoshiro plants aseptically propagated on the agar medium of Linsmaier and Skoog (Physiol. Plant. 18: 100–127, 1965) were used as the materials. These tissues were cut into segments of appropriate size and cultivated with Agrobacterium for 2 days. Thereafter, the tissues were placed on the agar medium of Linsmaier and Skoog (Physiol. Plant. 18: 100–127, 1965) containing 0.1 mg/l of indoleacetic acid, 1.0 mg/l of zeatin riboside, 100 mg/l of kanamycin and 250 mg/l of cefotaxime and cultured at 20° C. under illumination for 16 hours per day. The regenerated plants were subcultured on the agar medium of Linsmaier and Skoog (Physiol. Plant. 18: 100–127, 1965) containing 100 mg/l of kanamycin.

The grown transformants were cut into single sections and the sections were cultured in the liquid medium of Linsmaier and Skoog (Physiol. Plant. 18: 100–127, 1965) for 3 to 4 weeks (20° C., 16-hour illumination per day). The medium was then replaced with the liquid medium of Linsmaier and Skoog (Physiol. Plant. 18: 100–127, 1965) containing 80 g/l of sucrose and the plants were cultured at 20° C. in the dark for 4 or 5 weeks or more. The formed microtubers were washed with water, drained and placed in petri dishes, and stored at 20° C. or 4° C. in the dark. The plants growing on the agar medium of Linsmaier and Skoog (Physiol. Plant. 18: 100–127, 1965) were also subjected to the storage test in the dark at 20° C. or 4° C.

Luciferase activity was measured in accordance with a reference (Science 234: 856–859, 1986). To the plant tissues, an extraction buffer (100 mM potassium phosphate buffer (pH 7.5) containing 1 mM dithiothreitol) was added in an amount of 3–10 times the fresh weight of the tissues. The obtained mixture was ground and centrifuged (15,000 rpm, 5 minutes), and the supernatant was recovered as a crude extract. Then 50 μl of the crude extract and 100 μl of a buffer for measuring activity (36 mM glycylglycine buffer (pH 7.8) containing 1 mg/ml of bovine serum albumin, 20 mM magnesium chloride, 12 mM ATP) were mixed and 100 μl of 0.4 mM luciferin was added, followed by measurement of luciferase activity with a luminometer (Model 6100, Packard). The results are shown in Tables 7 and 8.

TABLE 7

Luciferase Activity in Leaves of Potato Transformants

| Line | Construct Used for Transformation | Storage Conditions | Luciferase Activity (cps/mg protein) |
| --- | --- | --- | --- |
| LUC1000-1-1 | pLUC210 (1000) | not stored | 25900 |
| LUC1000-1-1 | pLUC210 (1000) | 4° C., 4 weeks | 36000 |

TABLE 8

Luciferase Activity in Microtubers of Potato Transformants

| Line | Construct Used for Transformation | Storage Conditions | Luciferase Activity (cps/mg protein) |
| --- | --- | --- | --- |
| LUC101-2-1 | pLUC101* | not stored | 217 |
| LUC101-2-1 | pLUC101* | 20° C., 4 weeks | 166 |
| LUC101-2-1 | pLUC101* | 4° C., 4 weeks | 245 |
| LUC1001-1-1 | pLUC210 (1000) | not stored | 78200 |
| LUC1000-1-1 | pLUC210 (1000) | 20° C., 4 weeks | 23800 |
| LUC1000-1-1 | pLUC210 (1000) | 4° C., 4 weeks | 149000 |

*: construct lacking promoter, control

As is apparent from the tables, in the microtubers stored at a low temperature (4° C.) for 4 weeks, prominent increase in the activity was observed. Further, although the activity was lower than in microtubers, the activity in leaves was slightly increased at a low temperature. Therefore, it was proved that the DNA sequence (promoter sequence) which was the region from 2418th to 3541st nucleotide in the sequence shown in SEQ ID NO: 1 had a function to induce gene expression under low temperatures.

What is claimed is:

1. A DNA sequence comprising a nucleotide sequence from the first to the 3546th nucleotide in the nucleotide sequence shown in SEQ ID NO:1.

2. A DNA sequence comprising a nucleotide sequence from the 2418th to the 3541st nucleotide in the nucleotide sequence shown in SEQ ID NO:1.

3. A DNA sequence comprising a nucleotide sequence from the first to the 4120th nucleotide in the nucleotide sequence shown in SEQ ID NO:2.

* * * * *